(12) United States Patent
Khan et al.

(10) Patent No.: US 9,200,959 B2
(45) Date of Patent: Dec. 1, 2015

(54) TERAHERTZ SENSING SYSTEM AND METHOD

(71) Applicants: Mohammad J. Khan, Woburn, MA (US); Sumanth Kaushik, Belmont, MA (US); Jerry C Chen, Lexington, MA (US)

(72) Inventors: Mohammad J. Khan, Woburn, MA (US); Sumanth Kaushik, Belmont, MA (US); Jerry C Chen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 133 days.

(21) Appl. No.: 13/945,542

(22) Filed: Jul. 18, 2013

(65) Prior Publication Data

US 2014/0061473 A1 Mar. 6, 2014

Related U.S. Application Data

(63) Continuation of application No. 13/016,143, filed on Jan. 28, 2011, now Pat. No. 8,514,393.

(60) Provisional application No. 61/299,391, filed on Jan. 29, 2010.

(51) Int. Cl.
*G01J 3/42* (2006.01)
*G01N 21/3581* (2014.01)
*G01N 21/17* (2006.01)

(52) U.S. Cl.
CPC ............... *G01J 3/42* (2013.01); *G01N 21/3581* (2013.01); *G01N 2021/1793* (2013.01)

(58) Field of Classification Search
CPC ............. G01J 3/28; G01J 3/42; G01J 3/2823; G01N 21/3581; G01N 2021/1793; H01S 3/0092; H01S 5/0092
See application file for complete search history.

(56) References Cited

U.S. PATENT DOCUMENTS

| | | | |
|---|---|---|---|
| 3,610,932 A | 10/1971 | Morse et al. | |
| 3,629,602 A * | 12/1971 | Firester | ........................ 359/330 |
| 4,980,566 A | 12/1990 | Heilweil | |
| 7,339,718 B1 | 3/2008 | Vodopyanov et al. | |
| 7,501,627 B1 | 3/2009 | Herr | |
| 8,035,083 B1 | 10/2011 | Kozlov et al. | |
| 8,599,474 B1 | 12/2013 | Kozlov et al. | |
| 8,599,475 B1 | 12/2013 | Kozlov et al. | |
| 8,599,476 B1 | 12/2013 | Kozlov et al. | |

(Continued)

OTHER PUBLICATIONS

Onat et al., "A Solid State Hyperspectral Imager for Real-time Standoff Detection Using Shortwave Infrared Imaging", Proc. of SPIE, vol. 7310, pp. 1-11.*

(Continued)

*Primary Examiner* — Kara E Geisel
(74) *Attorney, Agent, or Firm* — Cooley LLP

(57) ABSTRACT

Disclosed herein are a system and corresponding method for sensing terahertz radiation. The system collects terahertz radiation scattered from a target and upconverts the collected radiation to optical frequencies. A frequency-domain spectrometer senses spectral components of the upconverted signal in parallel to produce a spectroscopic measurement of the entire band of interest in a single shot. Because the sensing system can do single-shot measurements, it can sense moving targets, unlike sensing systems that use serial detection, which can only be used to sense stationary objects. As a result, the sensing systems and methods disclosed herein may be used for real-time imaging, including detection of concealed weapons, medical imaging, and hyperspectral imaging.

20 Claims, 9 Drawing Sheets

(56) References Cited

U.S. PATENT DOCUMENTS

| | | | |
|---|---|---|---|
| 2002/0070349 | A1 | 6/2002 | Hoyt |
| 2004/0031906 | A1 | 2/2004 | Glecker |
| 2004/0150818 | A1* | 8/2004 | Armstrong et al. ........... 356/301 |
| 2007/0018103 | A1 | 1/2007 | DeCamp et al. |
| 2007/0152154 | A1 | 7/2007 | DeCamp et al. |
| 2008/0179527 | A1 | 7/2008 | Demers |

OTHER PUBLICATIONS

Chen, et al. "Terahertz Generation and Detection Using Nonlinear Frequency Conversion", 2010 23rd Annual Meeting of the IEEE Photonics Society (Formerly LEOS Annual Meeting), p. 169-70.

Chen, et al., "Ultrasenstive, Room Temperature Detection of THz Radiation Using Nonlinear Parametric Conversion", in Nonlinear Frequency Generation and Conversion: Materials, Devices, and Applications X, edited by Konstantin L. Vodopyanov, Proc. Of SPIE vol. 7917, pp. 791711-1 to 791711-12 (Apr. 1, 2011).

Chen, et. al., "Terahertz Generation and Detection Using Frequency Conversion", Lasers and Electro-Optics, 2009 and 2009 Conference on Quantum Electronics and Laser Science Conference CLEO/QELS Jun. 2-4, 2009, Baltimore,MD.

Chen, J.C., et al. "Terahertz Detection Using Optical Parametric Upconversion and Geiger Mode Avalanche Photodiodes", Lasers and Electro-Optics, 2008 and 2008 Conference on Quantum Electronics and Laser Science CLEO/QELS 2008. pp. 1-2.

International Preliminary Report on Patentability for PCT/US2011/022957 dated Jul. 31, 2012.

International Search Report of PCT/US2011/022957.

Kahn, et al., "Optical Detection of Terahertz using Nonlinear parametric upconversion" Dec. 1, 2008 / vol. 33, No. 23 / Optics Letters, pp. 2725-2727.

Khan, et al, "Optical Detection of Terahertz Radiation by Using Nonlinear Parametric Upconversion", Optics Letters, vol. 32, No. 22, Nov. 15, 2007, pp. 3248-3250.

Khan, et al. "Optical Detection of Terahertz Using Nonlinear Frequency Upconversion," in Conference on Lasers and Electro-Optics/Quantum Electronics and Laser Science Conference and Photonic Applications Systems Technologies, OSA Technical Digest Series (Optical Society of America, 2007), pp. 1-2.

Khan, et al., "Ultra-sensitive, room-temperatire THz detection based on parametric upconversion by using a pulsed 1550 nm Optical Source", IEEE Journal of Selected Topics in Quantum Electronics, vol. 17, No. 1, Jan./Feb. 2011.

US Notice of Allowance on 099477-0134 DTD Apr. 19, 2013.

US Office Action on 099477-0134 DTD Jan. 9, 2013.

US Office Action on 099477-0134 DTD Aug. 9, 2012.

* cited by examiner

TERAHERTZ SENSING SYSTEM AND METHOD

CROSS-REFERENCE TO RELATED PATENT APPLICATIONS

This application is a continuation under 35 U.S.C. §120 of U.S. application Ser. No. 13/016,143, filed on Jan. 28, 2011, which claims the benefit, under 35 U.S.C. §119(e), of U.S. Provisional Application No. 61/299,391, filed Jan. 29, 2010, which applications are incorporated herein by reference in their respective entireties.

GOVERNMENT SUPPORT

This invention was made with government support under Contract No. FA8721-05-C-0002 awarded by the U.S. Air Force. The Government has certain rights in the invention.

BACKGROUND

Terahertz waves possess several unique characteristics which make them desirable for a variety of remote sensing applications, including explosive detection, vibrometry, concealed weapons detection, hyper-spectral imaging, and medical imaging. For example, the reflection, scattering, and absorption spectra of a sample in the terahertz region of the electromagnetic spectrum give an indication of the sample's composition. Detecting terahertz radiation is extremely difficult, however, which is why a need exists for improved systems for and methods of sensing terahertz radiation.

SUMMARY

Embodiments of the present invention include a terahertz imaging system for and corresponding method of making spectroscopic measurements of a sample. Example systems include an upconverter configured to shift a measurement signal from a lower frequency, which is typically at terahertz frequencies (e.g., between about 100 GHz and about 10 THz), to a higher frequency, such as a frequency in the near infrared. A spectrometer operably coupled to the upconverter detects a spectrum of the measurement signal, which is representative of characteristics of the sample. The detected spectrum can then be used to derive information about spectroscopic characteristics of the sample. Because the spectrometer detects different spectral components of the measurement signal in a parallel manner, the system can measure moving samples and fast events.

Unlike terahertz imaging systems with serial architectures, terahertz imaging systems with parallel architectures can measure a complete spectrum once per pulse, resulting in much higher scan speeds (e.g., thirty times higher if the system measures thirty frequency components in parallel). The ability to measure a spectrum on "single shot" basis also means that the target need not be stationary and/or the terahertz sensor can be mounted on a moving platform. In addition, terahertz imaging systems with parallel architectures and high sensitivity can measure terahertz spectra at standoff, making them better-suited to rapid concealed weapons detection and other imaging applications.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments of the invention follows.

Terahertz sensing systems with parallel detection architectures and high sensitivity can measure terahertz radiation that is back-scattered from diffuse targets at standoff. In addition, the parallel detection architectures support target illumination with broadband terahertz sources, enabling measurements of spectroscopic signature of targets. These capabilities are enabled by a terahertz upconversion spectroscopy technique, described below, that uses optical detection techniques to perform sensitive measurements of terahertz radiation, which is very difficult to measure directly. First, received terahertz radiation is upconverted to an optical frequency. Next, the upconverted terahertz signal, or optical idler, is detected with a frequency-domain spectrometer, which may include many photon-counting detectors arranged in parallel. Because the detectors can count individual photons, they can make measurements with better sensitivity than those made with state-of-the-art, commercially available terahertz detectors despite loss due to upconversion. Parallel detection with photon counting detectors also enables terahertz sensing at a 5 meter standoff range, and may be used to perform standoff sensing at ranges of 20-30 meters and beyond.

Because the terahertz sensing described herein does ultra-sensitive, parallel detection, it is faster and more sensitive than other terahertz sensing. For example, it can completely measure the band of interest in a single shot. As a result, it can make spectroscopic measurements of targets moving in arbitrary manners, provided that the motion is not so fast as to move it out of the detection time window, currently set at 1 ns.

In contrast, current terahertz sensing systems measure terahertz spectra with Fourier transform Infrared (FTIR) spectrometers or time-domain spectroscopy (TDS) spectrometers, which measure spectra in a sequential fashion, i.e., one spectral or temporal measurement at a time. Because FTIR and TDS spectrometers operate in a serial manner, they are slow, so current terahertz sensing systems have to make many measurements to construct a single complete spectrum for one particular measurement plane. For example, sensing systems with time-domain spectrometers must measure many reflected, scattered, or transmitted terahertz pulses to construct a complete spectrum of the target. If the sample or sensor moves between or during individual measurements, the resulting spectrum may not represent the sample accurately. Thus, the distance to target must stay constant during a scan (i.e., the target must stay stationary during measurement), which is a major limitation for most imaging applications.

Terahertz Sensing with Upconversion Spectrometers

Figure 1:
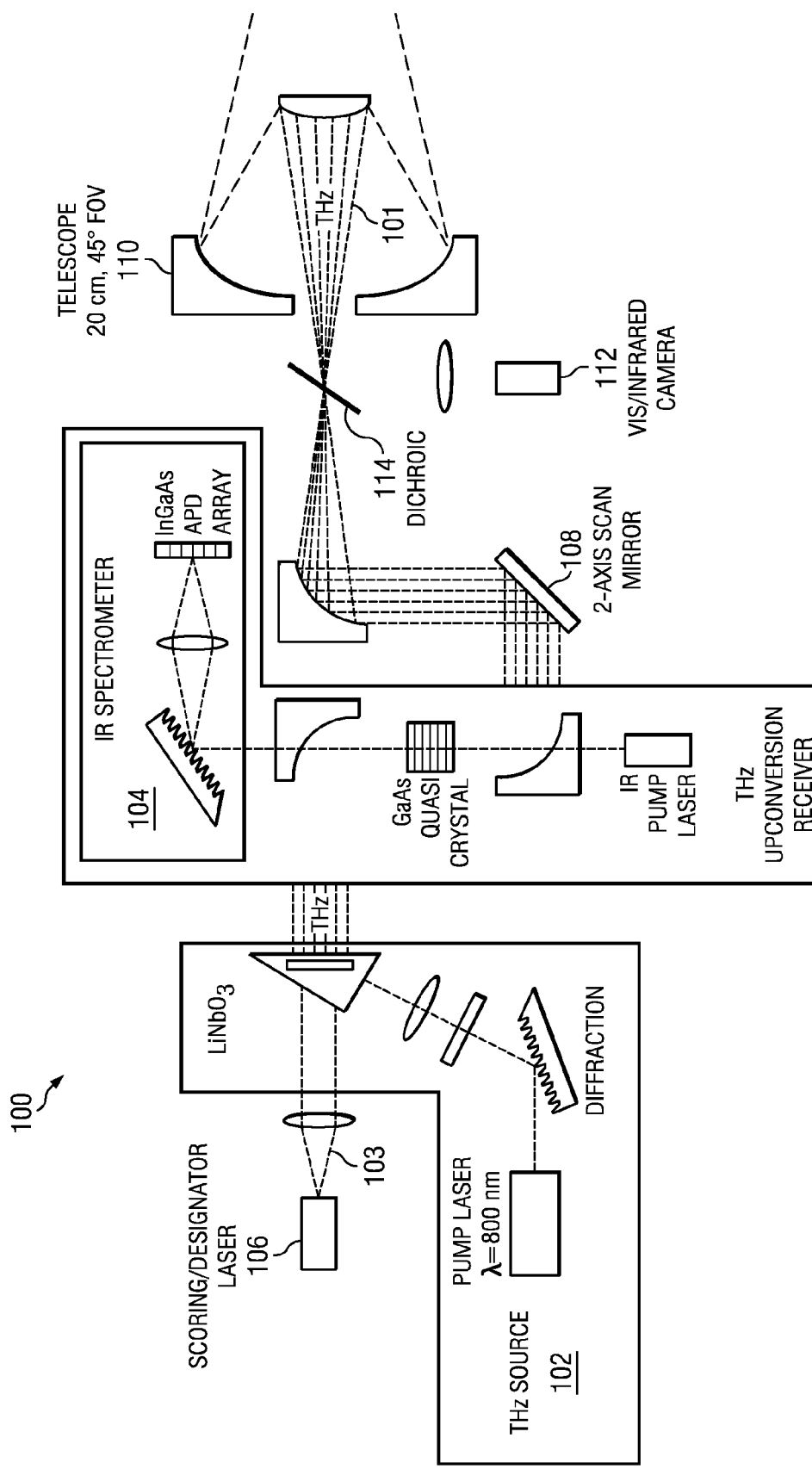
FIG. 1 is a block diagram of a terahertz sensing system according to an embodiment of the present invention.

FIG. 1 depicts a schematic of an example terahertz sensing system 100. It includes a high-power, pulsed terahertz source 102 and a terahertz upconversion spectrometer 104 arranged in a monostatic ladar configuration. The terahertz source 102 shown in FIG. 1 is a pulsed, high peak-power, broadband terahertz source developed by MIT; it is described in detail in K.-L. Yeh, J. Hebling, M. C. Hoffmann, and K. A. Nelson, "Generation of high average power 1 kHz shaped THz pulses via optical rectification," *Opt. Commun.*, 281, 3567 (2008), incorporated herein by reference in its entirety. Beside optical rectification, other suitable photoconductors include those reviewed by B. Ferguson and X.-C. Zhang, "Materials for terahertz science and technology," Nature Materials, vol. 1, September 2002, pp. 26-33, incorporated herein by reference in its entirety. Halogen lamps and synchrotrons that emit broadband terahertz radiation may also be used in the terahertz source 102. Other broadband terahertz sources can be employed for terahertz sensing so long as the spectrum of the terahertz source encompasses a spectroscopic feature of the sample.

The terahertz source 102 generates a terahertz beam 101 that the sensing system 100 can scan across a remote sample (not shown) along two axes with a two-axis scan mirror 108. A scoring/designating laser 106 generates a designator beam 103, which may be a visible beam, that is co-aligned with the outgoing terahertz beam 101. The terahertz beam 101 and the designator beam 103 are imaged or projected onto the sample with a telescope 110.

The terahertz beam 101 and the designator beam 103 reflect off the sample, producing back-scattered or back-reflected radiation that is collected by the telescope 110. A dichroic filter 114 separates the back-scattered/reflected terahertz radiation from back-reflected visible and infrared light, which is directed to a visible/infrared camera 112 that can be used to align the terahertz beam 101 in conjunction with the designator beam 103. The back-scattered/reflected terahertz radiation propagates through the dichroic filter 114 to a terahertz upconversion spectrometer 104 that upconverts and then resolves the upconverted terahertz radiation into separate frequency components and detects the frequency components in parallel.

Figure 2:
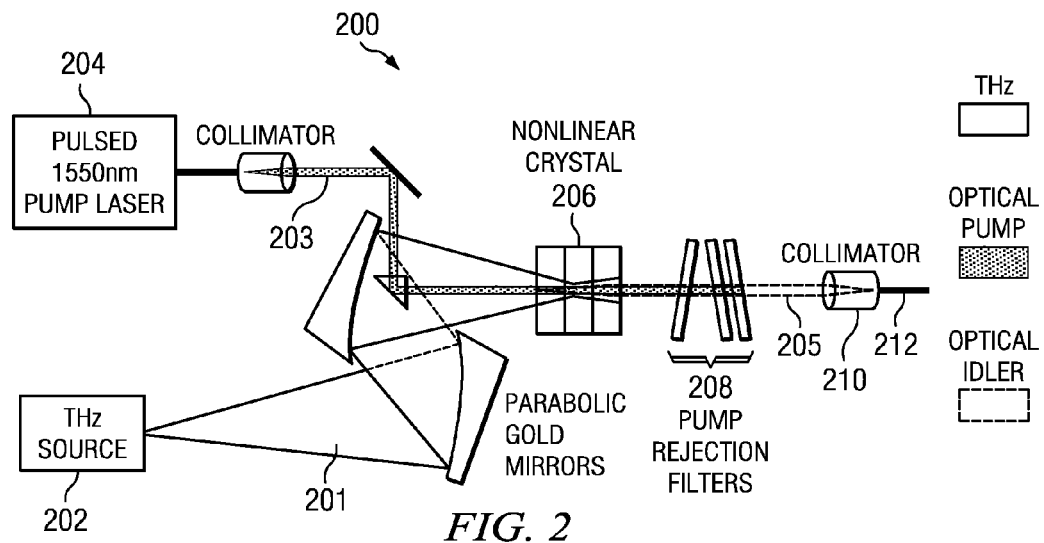
FIG. 2 is a block diagram of a terahertz upconversion receiver that upconverts a measurement signal from terahertz frequencies to optical frequencies by mixing the measurement signal with an optical pump beam in a nonlinear crystal.

FIG. 2 shows a terahertz upconverter 200 suitable for use as a first stage of the upconversion spectrometer 104 shown in FIG. 1. Parabolic, gold-coated mirrors focus a terahertz signal beam 201 from a terahertz source 202, such as a sample illuminated by another terahertz beam, into the volume of a nonlinear crystal 206. An optical pump beam 203 from a high-power, pulsed optical source 204 is co-propagated with the terahertz signal beam 201 in the nonlinear crystal 206, causing a nonlinear interaction between the terahertz signal beam 201 and the optical pump beam 203. The nonlinear interaction between the terahertz beam 201 and the optical pump beam 203 produces an optical idler beam 205 at a frequency equal to the difference in frequency between the terahertz and optical beams 201 and 203. The upconversion process, also known as difference-frequency generation, has a quantum efficiency gain as low energy terahertz photons are converted to high-energy optical idler photons. The resulting optical idler beam 205 is separated from the optical pump beam 203 with thin-film dielectric filters 208 and coupled into a single-mode fiber 212 using a collimator 210. Detection of the optical idler beam 205 provides a direct measure of the incident terahertz signal 201 due to the linear relationship between the power of the optical idler 205 and the terahertz beam 201.

The theoretical idler power can be estimated using the following expression:

$$P_{Idler} = \frac{8\pi^2 (d_{eff})^2 L^2 I_{Pump} T_{Filters} T_{Fresnel}}{c\varepsilon_o n_T n_I n_P \lambda_I^2} \times \mathrm{sinc}\left(\frac{\Delta k L}{2}\right)^2 P_{THz},$$

where $d_{eff}$ is the effective nonlinearity, L is the length of the crystal, $I_{pump}$ is the pump intensity, and $n_T$, $n_I$, and $n_P$ are the refractive indices at the THz, idler, and pump frequencies, respectively. $\Delta k = k_P - k_I - 1_T$ is the wave-vector mismatch. $T_{Filters}$ is the combined insertion loss of the filters, and $T_{Fresnel}$ is the transmission coefficient of the idler at the GaAs crystal interface.

FIG. 2 shows one of several possible configuration geometries suitable for use in an upconversion receiver. There is flexibility in the configuration geometry; in fact, the terahertz sensing system used to generate the experimental results described below uses a different geometry (FIG. 6) to co-propagate the optical pump beam with the THz radiation that is back-reflected from the target.

Figure 3:
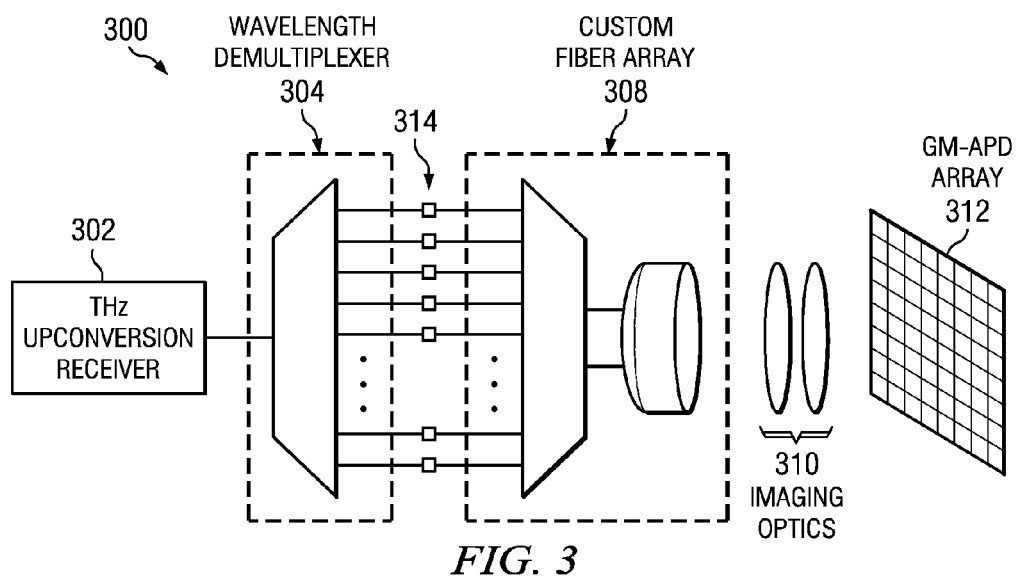
FIG. 3 is a block diagram of a terahertz upconversion spectrometer according to an embodiment of the present invention.

FIG. 3 shows a schematic of an upconversion spectrometer 300 suitable for detecting an optical idler beam generated by a terahertz upconversion receiver 302, which may be identical to the upconverter 200 shown in FIG. 2. Like the upconverter 200 of FIG. 2, the receiver 302 shown in FIG. 2 upconverts incoming terahertz radiation (not shown) to the optical frequency regime using a nonlinear crystal. The resulting upconverted signal is then coupled into an infrared spectrometer 300 that includes a fiber-coupled wavelength-division demultiplexer 304 (such as a diffraction grating device, arrayed waveguide grating, etc.), fibers 314, custom fiber array 308, imaging optics 310, and detector array 312, such as an ultra-sensitive, photon-counting Geiger-mode avalanche photodiode detector array. The wavelength demultiplexer 304 maps each spectral component of the optical signal to a respective fiber 314, and the custom fiber array 308 maps each fiber into a different spatial position. Imaging optics 310 image each fiber in the fiber array 308 onto a corresponding detector in the detector array 312 such that each detector senses one spectral component of the upconverted terahertz beam.

In one example, the demultiplexer 304 can separate the upconverted terahertz signal in forty channels arrayed on a frequency grid with 25 GHz spacing, where each channel has a 3 dB linewidth of 12.5 GHz. The forty output channel fibers used to accommodate the forty frequency channels are mated with a custom 6×7 fiber array 308, with two channels left unused. The fiber array 308 has attached lenslets and delivers 6×7 collimated beams on a 250 µm grid. The imaging optics 310—two simple lenses—demagnify the fiber array grid spacing and match it to the 100 µm grid spacing of the Geiger-mode avalanche photodiode array 312.

The detector array 312 transmits signals representing the detected spectral components to a processor and memory (not shown), which can be used to compare the detected spectral features to a stored indication of the spectrum of the emitted terahertz beam. Differences between the detected spectral features and the spectrum of the emitted terahertz beam provide an indication of spectroscopic features of the sample. Because the detector array 312 captures a complete spectrum for every transmitted pulse, the system can do real-time imaging of moving targets, including targets moving in an arbitrary manner.

Even though the sensing system, upconversion receiver, and spectrometer shown in FIGS. 1-3 use specific demultiplexers, detector arrays, etc., the general terahertz sensing system architecture offers a lot of flexibility. For example, alternative demultiplexers, such as arrayed waveguide gratings, fiber Bragg gratings, and virtually imaged phased arrays can also be employed in the spectrometer. Similarly, fiber-based devices can be replaced by free-space devices, such as diffraction gratings and prisms, and vice versa. For example, using a free-space demultiplexer in conjunction with a 1D detector array eliminates the need for a custom fiber array 308 and fibers 314. Likewise, suitable detector arrays include Geiger-mode avalanche photodiode arrays, photon multiplier tubes, charge coupled devices, PIN photodiodes, and other optical detector arrays. Moreover, heterodyne detection configurations can employed instead of the direct detection scheme shown in FIG. 3 to improve the measurement sensitivity.

Terahertz Upconversion with Second-Order Nonlinear Materials

The noise performance of the terahertz receiver improves linearly with the terahertz-to-optical conversion efficiency, which depends on the strength of the nonlinear interaction supported by a second-order nonlinear medium (e.g., crystal 206 in FIG. 2). The strength of the interaction depends, in part, on the size of the second-order nonlinear coefficient and on propagation and reflection losses of the second-order nonlinear material. GaAs is an excellent choice for a second-order nonlinear crystal because of its large second-order nonlinearity and low losses at terahertz and infrared frequencies; however, other nonlinear materials (crystals, polymers, liquids, gas etc.) can also be used.

The conversion efficiency is also quadratically related to the length of nonlinear medium, so doubling the length of the nonlinear media quadruples the conversion efficiency. Increasing the length of the crystal beyond the coherence length does not lead to the generation of more idler (upconverted terahertz beam), however, because the idler and terahertz waves gradually walk out of phase and eventually recombine to form a beam at the pump frequency. This effect, known as "walk off," causes the amplitude of the emitted idler beam to oscillate as a function of bulk crystal length. In general, the length corresponding to a slip in phase of π between the pump, idler, and terahertz fields is called the "coherence length."

Fortunately, walk off can be overcome with phase-matching and quasi-phase-matching (QPM) techniques. These techniques effectively eliminate or reduce the separation in phase between the pump, idler, and terahertz waves as the waves propagate through the nonlinear medium. In QPM crystals, including QPM GaAs, the polarity of the nonlinearity reverses when the idler and terahertz beams have slipped out of phase by π radians. This polarity reversal restores the phase slip to zero so the idler amplitude can continue to grow. This polarity reversal is accomplished by periodically poling or stacking crystals with alternating orthogonal orientation every coherence length.

Figure 4:
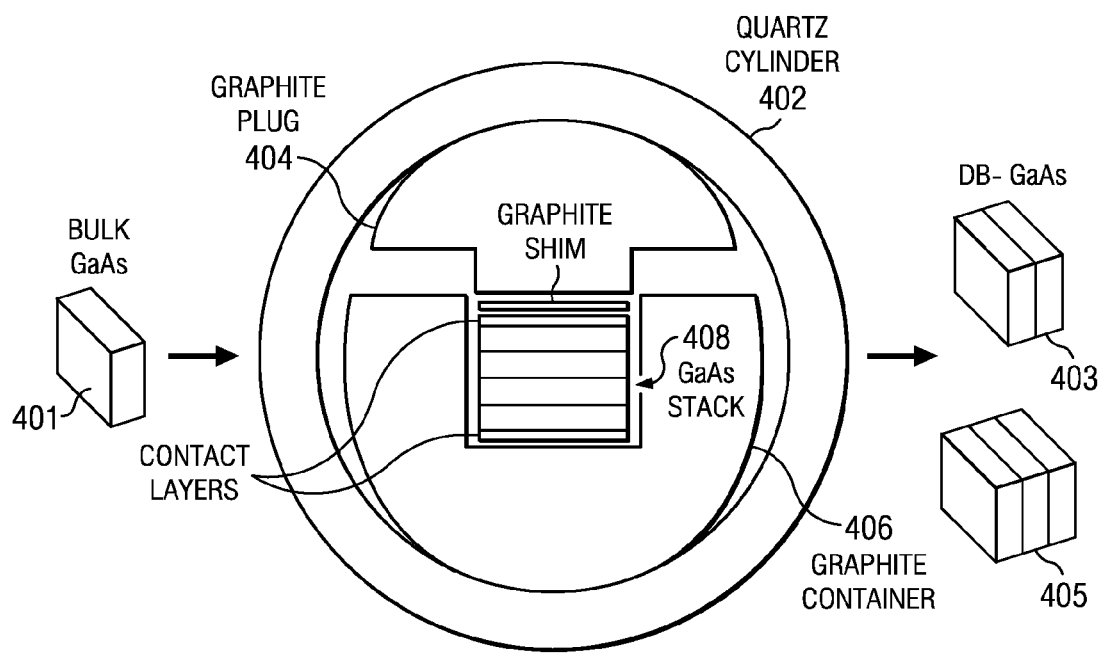
FIG. 4 illustrates the diffusion bonding process used to create quasi-phase matched (QPM) GaAs crystals suitable for use in terahertz upconversion receivers. Bulk crystals and other forms of phase-matched materials may also be employed.

FIG. 4 illustrates a diffusion-bonding process used to make QPM GaAs crystals 403 and 405 from bulk GaAs crystals 401. Bulk GaAs crystals 401 are arranged in a GaAs wafer stack 408 with layers whose thickness is about equal to the coherence length. The crystallographic axes of adjacent layers are oriented in orthogonal directions to reverse the polarity of the crystal nonlinearity. The wafer stack 408 is put inside a graphite container 406 that is shimmed with a graphite plug 404 to fit tightly into a quartz cylinder 402 and then heated to 700 degrees Celsius. Differential thermal expansion of the graphite 404, 406 and quartz 402 compresses the wafer stack 408 into atomic contact and fuses the GaAs pieces in the stack 408 together. After bonding, the exposed surfaces of the resulting QPM crystals 403, 405 are re-polished to provide optically flat surfaces.

Alternatively, besides diffusion bonding, QPM crystals can be formed via optical contact and orientation patterning as described in J. E. Shaar et al., *IEEE Journal of Selected Topics in Quantum Mechanics*, vol. 34, 2008, pp. 354-362, incorporated herein by reference in its entirety. Phase-matched crystals can also be made from periodic poling, total internal reflection and orientation patterning with varying periods and with waveguides, as reviewed in D. S. Hume and M. M. Fejer, *C. R. Physique*, vol. 8, 2007, pp. 180-198, incorporated herein by reference in its entirety.

Figure 5:
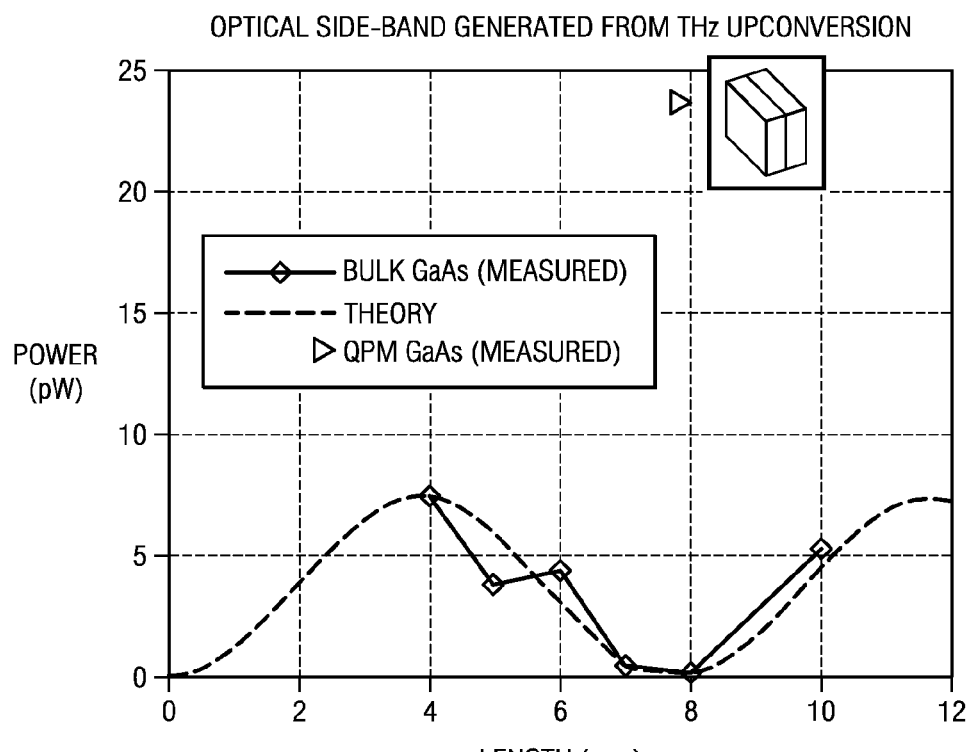
FIG. 5 is a plot of optical idler power versus crystal length for a theoretical bulk GaAs crystal (dashed line), an actual GaAs bulk crystal (diamonds), and an actual two-layer QPM GaAs crystal (triangle).

FIG. 5 is a plot of theoretical and experimental data of optical idler (upconverted terahertz radiation) power versus crystal length for bulk and QPM GaAs crystals. The dashed line is the theoretical idler power for a bulk GaAs crystal; it oscillates with a period of about eight millimeters. Experimental measurements of idler power produced with a bulk GaAs crystal, indicated by diamonds, agree very well with theory and do not exceed more than 10 pW. A two-layer QPM GaAs crystal exhibits an idler power of almost 25 pW (triangle) for a crystal length of about eight millimeters. The improvement in conversion efficiency with QPM is near 5 dB and close to the theoretical limit of 6 dB.

In addition, phase-matching can be achieved by angle-tuning a birefringent material or by confining the nonlinear interaction within a waveguide whose effective index is designed such that phase walkoff between the pump, idler, and terahertz beams is minimized. Confinement and resonant conversion also increase the conversion efficiency by increasing the intensity of the interacting waves.

Coatings for Second-Order Nonlinear Materials

Nonlinear materials, including QPM crystals, may be coated with anti-reflection coatings that suppress reflections at near-infrared frequencies (i.e., at wavelengths near 1550 nm) and that have minimal losses at terahertz frequencies. These anti-reflection coatings allow most of the optical pump light into the crystal and most of the idler light out of the nonlinear crystal. Unlike other coatings, which may absorb incident terahertz beams, the coatings absorb only negligible amounts of radiation at terahertz frequencies. Example coatings are made of layers of aluminum oxide and tantalum pentoxide. The high transmissions at optical frequencies and low absorption at terahertz frequencies result in an additional 2.5 dB of improvement in upconversion efficiency, which in turn results in a room-temperature noise sensitivity of 78 fW/Hz$^{1/2}$ at modest pump intensities.

Optical Pumping

The conversion efficiency scales linearly with the optical pump intensity. If the terahertz beam is continuous wave (CW), using a CW optical pump enables continuous collection of the spectrum. Pulsing the pump enables greater pump intensities and greater conversion efficiency, but causes the idler to pulse, resulting in pulsed spectrum information.

Similarly, pulsed terahertz radiation can be used with either CW or pulsed optical pump. Having a CW pump makes temporal alignment of the pump and terahertz very easy, but optical pump power that does not temporally overlap the terahertz radiation may be wasted. Using a pulsed optical pump requires careful temporal alignment of the pump and terahertz. Since the pump and terahertz both may have jitter, it is advantageous to make the pump pulse a bit wider than the terahertz pulse width, This increased width also gives some tolerance to the temporal alignment, too. Temporal alignment may be improved by transmitting a pulsed designator beam to the target along with the terahertz beam. A detector that senses this designator can be used to estimate the terahertz beam's arrival time on the upconversion crystal. Alternatively, the arrival time can be estimated if the distance traveled by the terahertz beam is known. Also, the pump's width and delay can be varied to find temporal overlap.

Parallel sensors can handle practically arbitrary motion from the sensor platform and spectroscopic target. For example, a parallel sensor can measure targets whose positions relative to the sensor change by $L=v \times t_i$, where v is the relative velocity between the sensor and target and $t_i$ is the integration time needed to make a measurement. The detector array should be able to measure during a time window that exceeds 2 L/c, where c is the speed of light (terahertz radiation) in the medium between the target and sensor. The idler pulse width should be smaller than the 2 L/c for best power efficiency. So, fast movements can be accommodated with a larger temporal gate or measurement window.

Example CW pumps include DFB lasers and Fabry-Perot diodes with fixed or tunable wavelengths. CW pump sources may be amplified with erbium doped fiber amplifiers. Suitable pulsed sources include CW sources modulated by external lithium niobate modulators, gain-switched semiconductor optical amplifiers, and mode-locked lasers. Alternatively, pulsed pump light can be produced by directly modulating a DFB laser. Pulsed sources may also be amplified with erbium doped fiber amplifiers. In experimental examples, mitigation of nonlinear fiber effects, such as stimulated Brillouin scattering and self-phase modulation, allows the realization of 1550 nm pumps with peak powers exceeding 10 kW. Tunable optical pumps allow tuning of the idler wavelength to match the spectrometer's wavelength. Alternatively, the spectrometer can be tuned to match a fixed pump wavelength by re-aligning a grating or prism or by heating the WDM demultiplexer.

Experimental Demonstration

Figure 6:
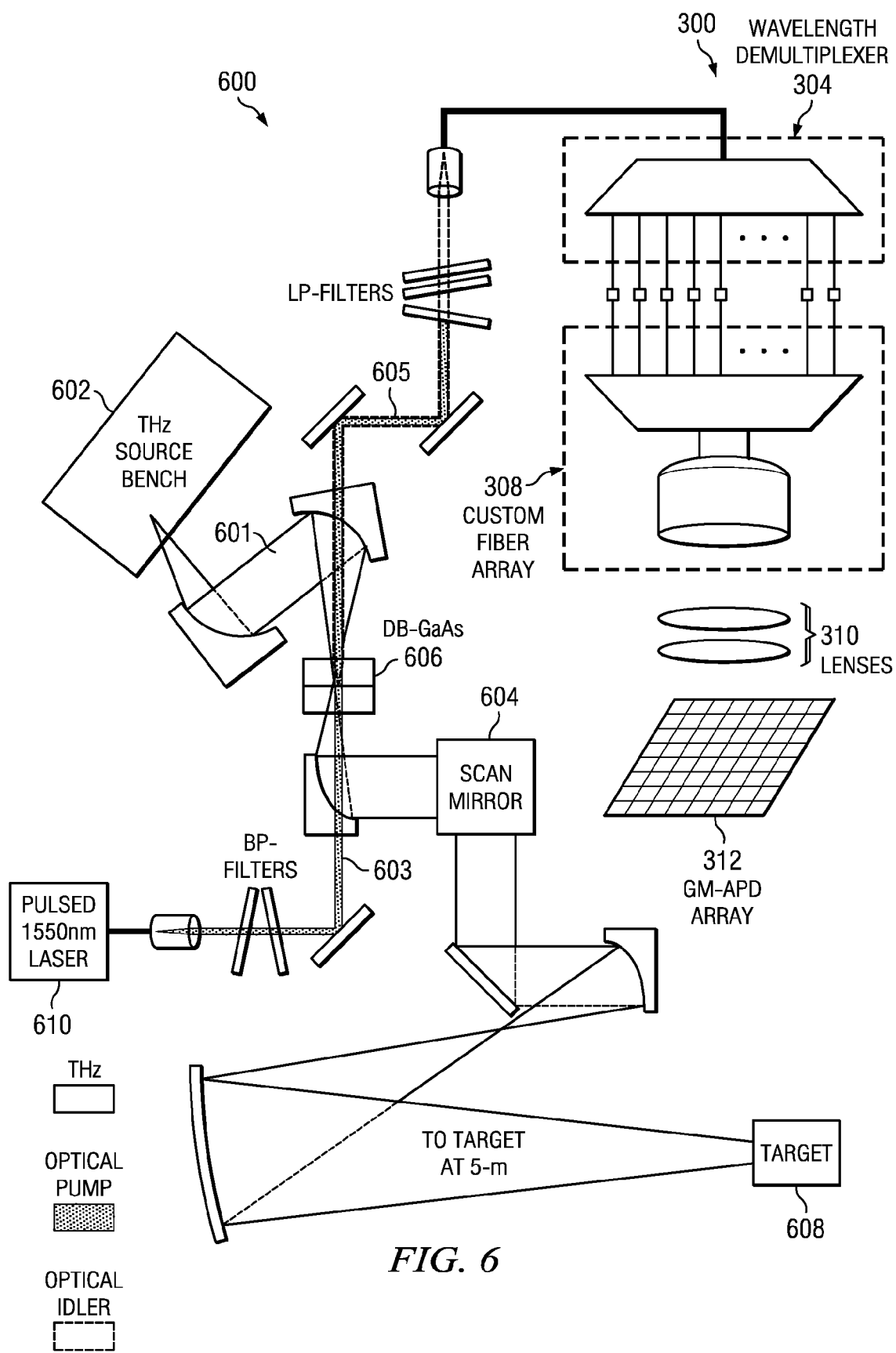
FIG. 6 is a block diagram of a laboratory implementation of a terahertz sensing system according to an embodiment of the present invention.

FIG. 6 shows a laboratory implementation 600 of a terahertz sensing system. Like the system 100 shown in FIG. 1, the implementation 600 includes a terahertz source that generates an outgoing terahertz beam 601. The outgoing terahertz beam 601 propagates through a QPM GaAs crystal 606 before being scanned across a target 608 with a scan mirror 604. The outgoing terahertz beam 601 is reflected from the target, which is about five meters away; the back-scattered THz radiation is focused into the nonlinear crystal 606, where it interacts with an optical pump beam 603 from a pulsed pump laser 610. The collected, back-reflected terahertz radiation mixes with the pump beam 603 to produce an optical idler beam 605 whose spectrum mimics that of the terahertz radiation. A spectrometer 300, described above, resolves the idler beam 605 into its frequency components and detects the frequency components in parallel with a detector array 312. Because detection occurs in parallel, the system can detect the entire spectrum in a single shot.

Figure 7:
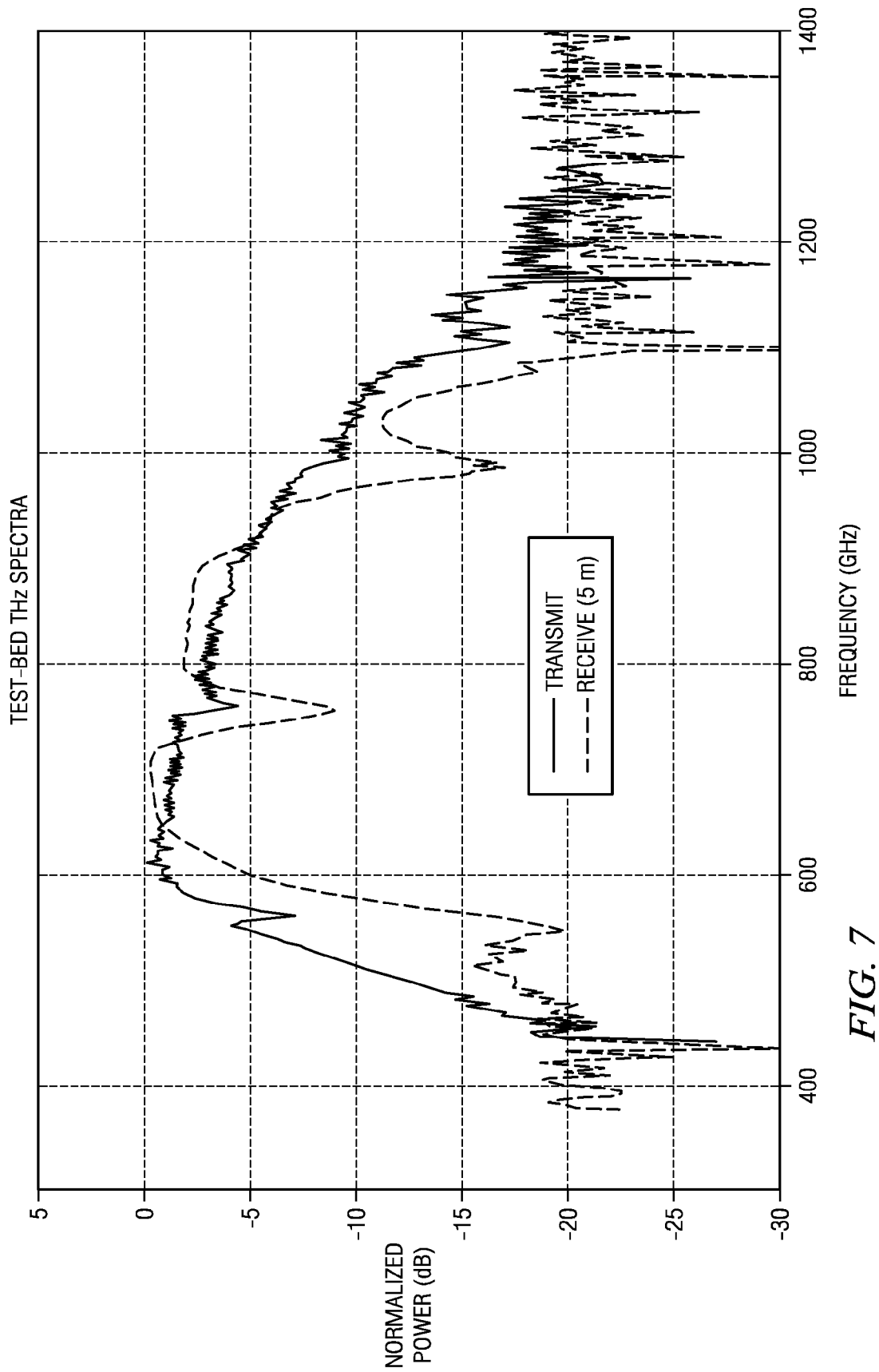
FIG. 7 is a plot of terahertz transmit and receive spectra measured with the system shown in FIG. 6. In this measurement, the upconverted signal was directly connected to and measured with a commercial optical spectrum analyzer (OSA).

FIG. 7 shows the measured spectrum of transmit and receive terahertz pulses from a target at a standoff of five meters. In this measurement the terahertz signal was reflected from a retro-reflector; the upconversion stage was directly connected to an optical spectrum analyzer to measure the terahertz spectrum. The wavelength of the measured signal is converted to frequency (in THz), then subtracted from the optical pump frequency (in THz) to get the received terahertz spectrum in THz. FIG. 7 shows that upconversion enables measurement of a terahertz spectrum using standard laboratory test equipment on an optical spectrum analyzer.

Separate measurements show the idler signal strength for terahertz radiation back-scattered from a variety of diffuse and specular targets at a standoff distance of five meters. These measurements were made in serial fashion with a single Geiger-mode avalanche photodiode coupled to a tunable optical filter instead of the 40-channel architecture shown in FIG. 6. The avalanche photodiode counted the number of one-nanosecond intervals in one second that contained photons scattered back from the target. Table 1 shows the returns signal counts from the various targets:

| Target | Average Counts |
| --- | --- |
| Retro-reflector | 81800 |
| Flashlight | 90 |
| Laboratory notebook | 72 |
| Wooden box | 71 |
| Plastic THz attenuator | 60 |
| Hand | 20 |

The sensitivity, or noise equivalent power, of a single channel of the terahertz upconversion spectrometer is 78 fW/Hz$^{1/2}$; this exceeds the performance of liquid-helium-cooled bolometers and electro-optic sampling detector used for detecting terahertz waves by nearly 15 dB. The spectrometer channel has a timing resolution of 1 ns, which far exceeds that of any commercial terahertz direct detector.

Sensor Dynamic Range

Figure 8:
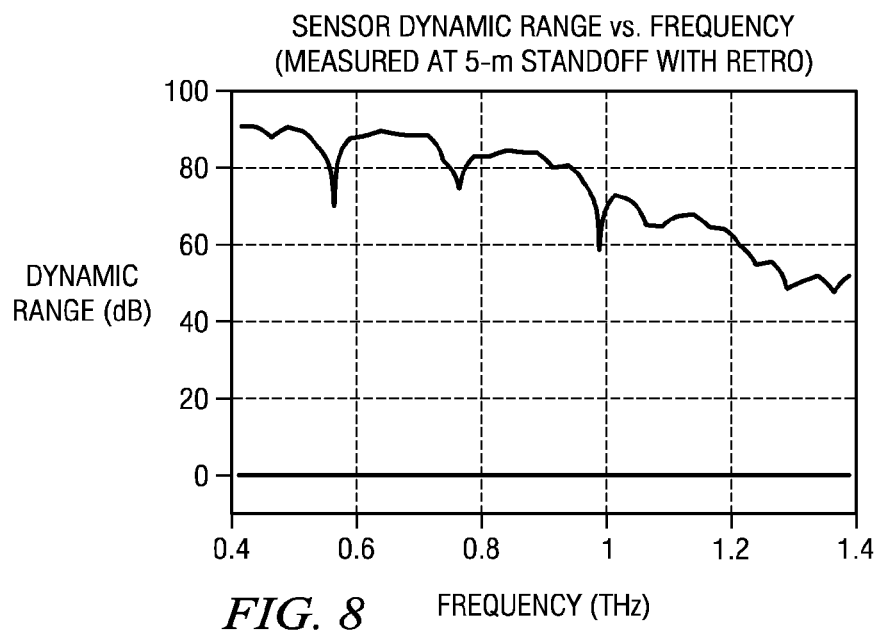
FIG. 8 is a plot of sensor dynamic range versus frequency measured using the Geiger-mode APD detector; the dynamic range exceeds state-of-art by at least 30 dB showing capability of system.

FIG. 8 is a plot of sensor dynamic range versus frequency measured using the laboratory implementation 600 of FIG. 6. In this particular measurement the THz signal was reflected from a retro-reflector at a standoff distance of five meters. The upconversion stage was connected via channel demultiplexer to an optical switch and then to a single-element, Geiger-mode APD detector via an attenuator rather than using the GM-APD array. FIG. 8 shows that the dynamic range exceeds 90 dB, which is at least 30 dB better than commercial state-of-art THz spectrometer systems. The horizontal line at 0 dB shows the detection limit or noise floor of the laboratory implementation 600. The large measured dynamic range demonstrates a highly sensitive sensor capable of spectrally resolved standoff measurements of targets at distance. The frequency coverage of 1 THz is limited due to the use of a 40-channel wavelength demultiplexer (DMUX) and can be easily increased by using a higher channel count DMUX. The frequency resolution of the laboratory implementation 600 is 25 GHz and this too can be easily enhanced.

Imaging Behind Barriers

Figure 9A:
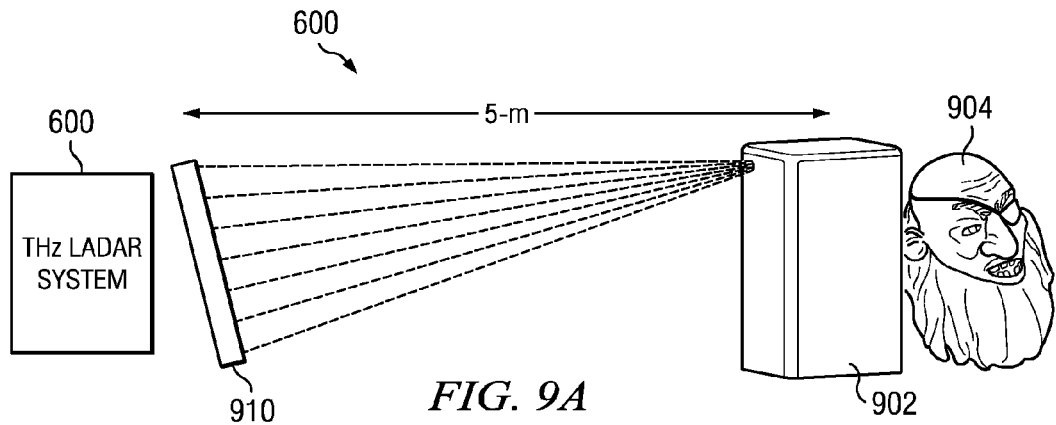
FIGS. 9A and 9B illustrate standoff imaging (5-m) of a pirate mask obscured from view by recycling bin. Change detection enables identification of C4 explosive on the ear of the pirate mask.

FIG. 9A illustrates standoff imaging of a diffuse object (pirate mask 904) behind a barrier (recycling bin 902) using the laboratory implementation 600 of FIG. 6. This is done by using a scan mirror 910 to raster scan the THz beam across the target area. This particular measurement was made with a single THz channel centered around 820 GHz with a 12.5 GHz bandwidth. It should be understood by a person of ordinary skill in the art that this measurement can be extended to other frequencies to get a more complete spectroscopic image. In the example embodiment of FIG. 9A, the reflective mirror is positioned and moved to create a scanner 910. The terahertz beam can also be deflected or scanned with risley prisms or metamaterial beam steerers. The optical pump that generates the THz in the present embodiment 102 can also be deflected, which leads to a deflected terahertz beam.

Figure 9B:
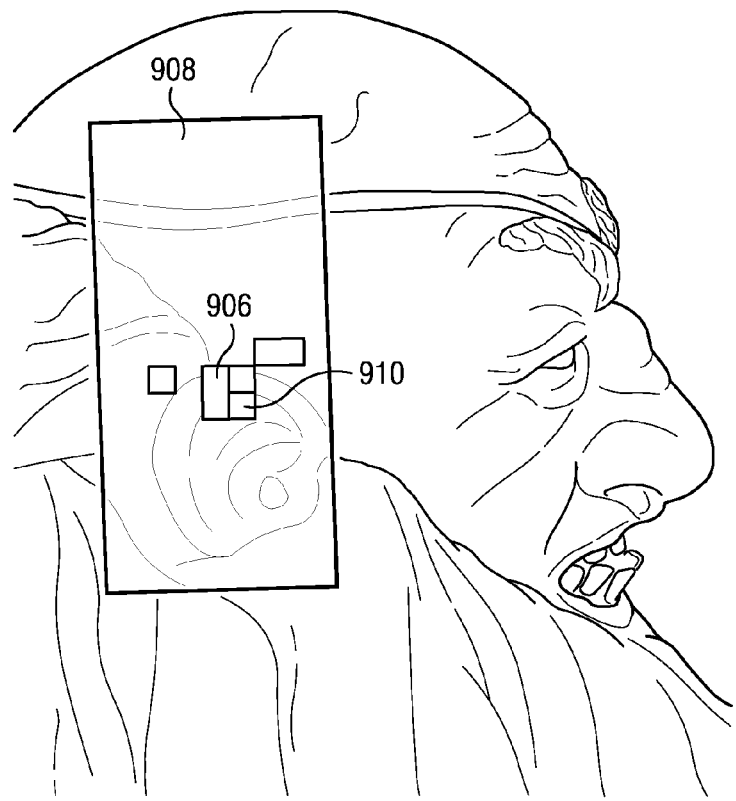

FIG. 9B shows a photograph of a mask. A large rectangular block 908 marks an area scanned by the terahertz sensor. A smaller square block 910 shows the location of detection of a piece of C4 explosive 906 placed on the mask's ear. When there is no C4, two scans are taken and a calculation is made to determine the scan's mean and standard deviation. Much of the standard deviation results from speckle noise. When C4 is present, another two scans are taken and further calculations are made to determine its mean and standard deviation. Differences between the two averages are identified and any differences smaller than the standard deviation are ignored. This change detection can easily locate the C4 explosive 906. Averaging the scans and thresholding out the noise (i.e., the standard deviation of two scans) mitigate speckle. The sensor's large dynamic range also enables faster scanning at longer standoff ranges.

Standoff THz Spectroscopy

Figure 10A:
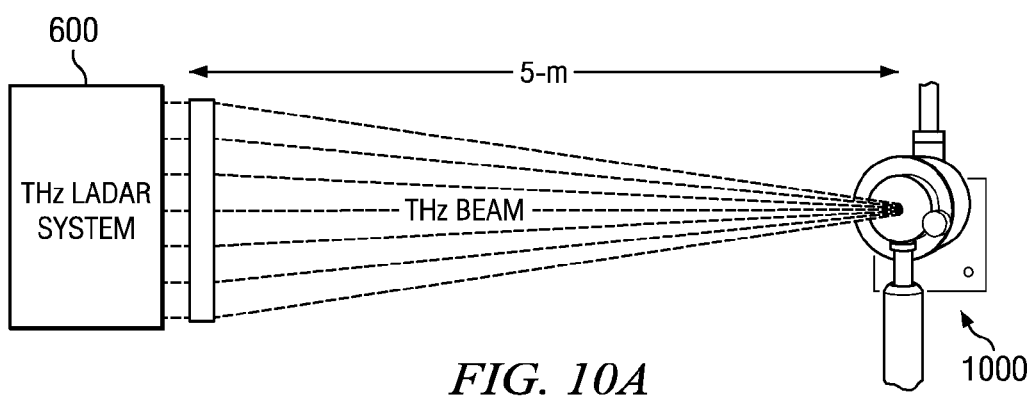
FIGS. 10A and 10B illustrate standoff spectroscopy at 5-m on dilute RDX pellets placed in front of a retro-reflector.
Figure 10B:
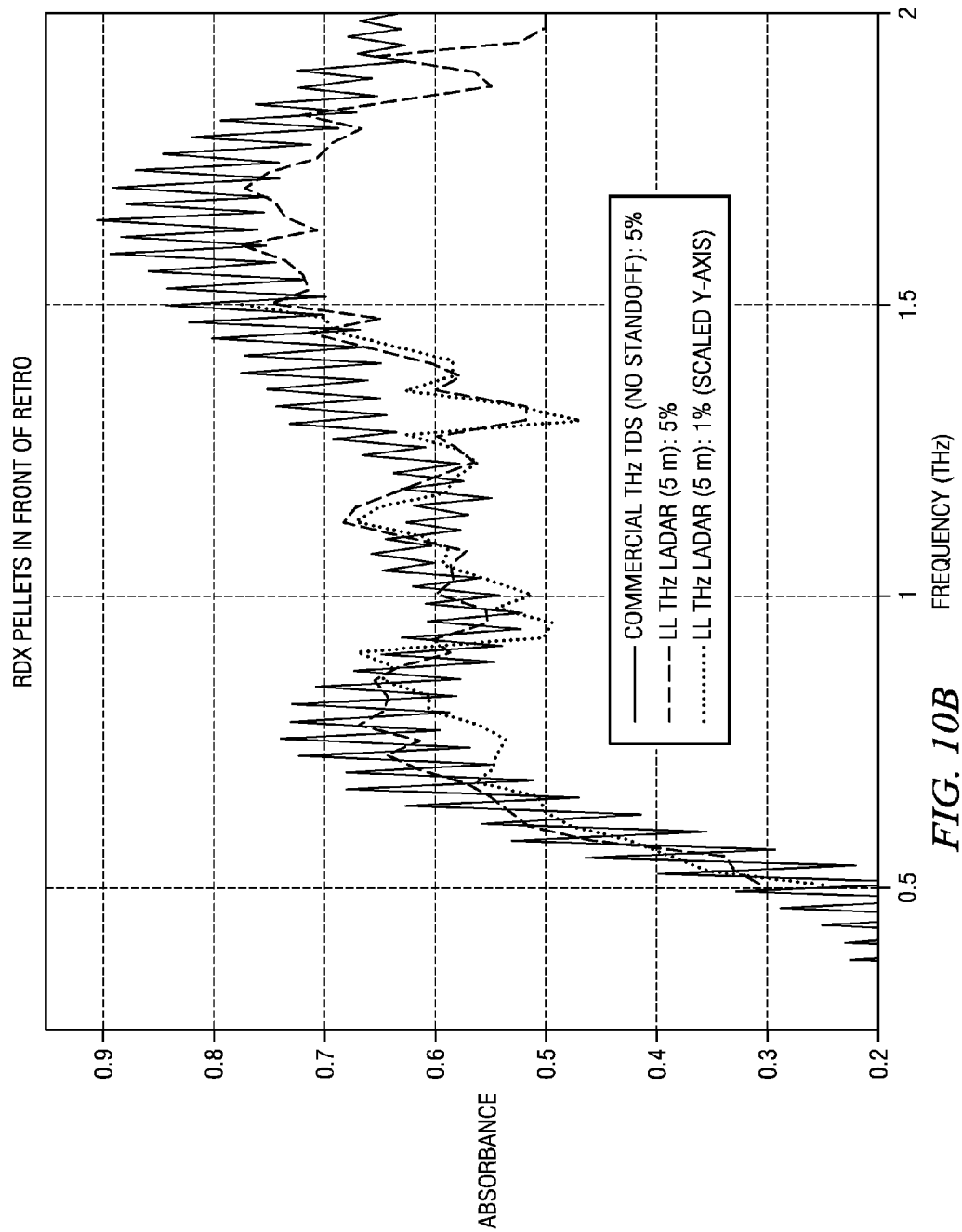

FIG. 10A shows spectroscopy of explosives 1000 at a standoff of five meters using the laboratory implementation 600 of FIG. 6. Several different compounds were measured, including RDX, DNT (a derivative of TNT), and lactose. In the case of RDX and DNT, the pelletized samples were placed in front of a retro-reflector. FIG. 10B shows the measured absorbance spectra of the dilute pellets down to 1% by weight of RDX. As can be seen from FIG. 10B, there is excellent agreement between the measured spectra at 5 m standoff with the inventive THz ladar system and measurements made, at no standoff, using a commercial state-of-art THz time-domain spectrometer. FIG. 10B also shows spectral coverage all the way out to 2 THz thanks to the replacement of the 40-channel DMUX 304 (FIG. 6) in the laboratory implementation 600 with a tunable filter. The results achieved with this substitution confirm that it is easy to extend the frequency coverage of the inventive THz ladar system with simple hardware changes. This is possible because the novel design enables a demonstrated ultra-sensitive detection capability.

Figure 11:
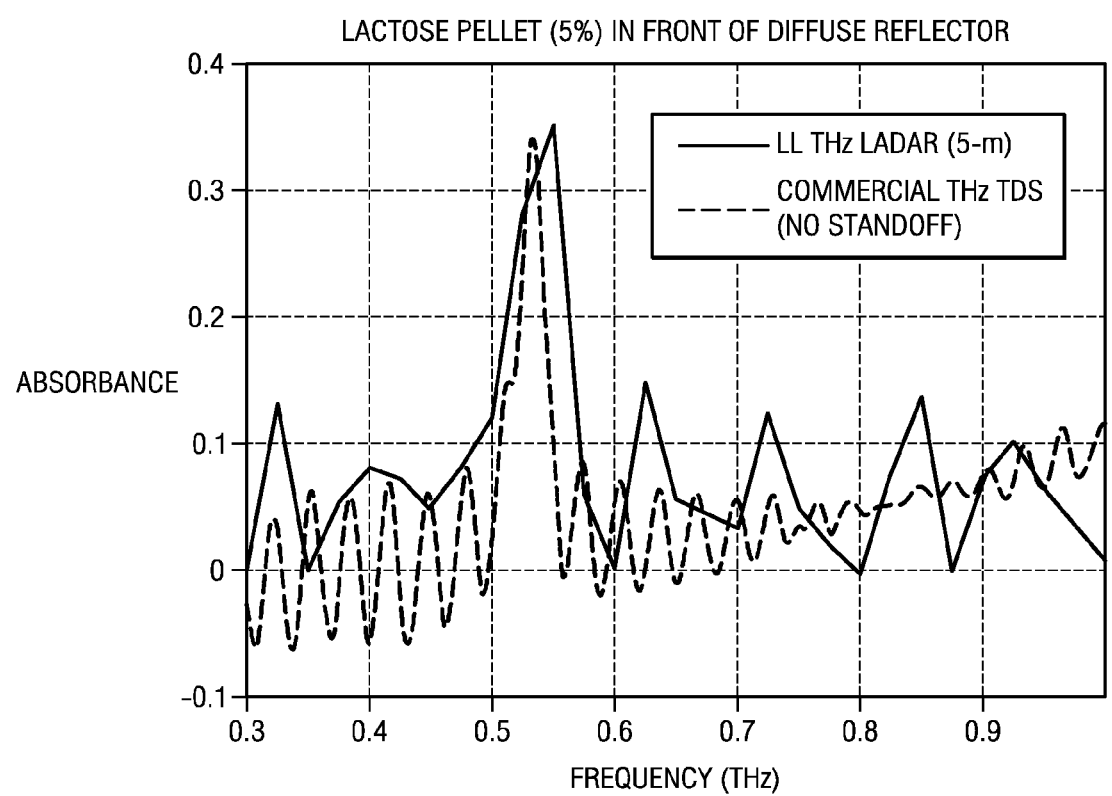
FIG. 11 is a plot of a measured absorbance spectrum of a dilute lactose pellet placed in front of a diffuse reflector (spectralon) taken at 5-m standoff using the novel THz spectroscopic ladar.

FIG. 11 shows the absorbance spectrum of a dilute (5% by weight) lactose pellet positioned in front of a piece of spectralon made using an inventive THz ladar system. The spectralon is a diffuse reflector; it is a Lambertian surface and scatters the light in a wide cone angle. The part of the THz back-scattered radiation intersecting the receive optic was detected and frequency resolved. The lactose feature is clearly visible and agree well with a near-in (no standoff) measurement made with a state-of-art THz time-domain spectrometer. The commercial spectrometer does not have standoff capability. The spectralon was rotated to perform speckle averaging. Other ways to mitigate speckle induced noise include averaging over different spatial modes, frequencies, look angles, etc. To the best of our knowledge, this is the first-ever demonstration of standoff THz spectroscopy off a diffuse scatterer.

While this invention has been particularly shown and described with references to example embodiments thereof, it will be understood by those skilled in the art that various changes in form and details may be made therein without departing from the scope of the invention encompassed by the appended claims. For example, terahertz sensing may be performed in bistatic or transmission geometries in addition to the reflection geometries of FIGS. 1 and 6.

The invention claimed is:

1. A system for sensing a signal beam from a sample at a first frequency, the system comprising:
   a difference-frequency generator to mix the signal beam with an optical pump beam so as to produce an optical idler beam at a second frequency equal to a difference between the first frequency and a frequency of the optical pump beam;
   a filter, in optical communication with the difference-frequency generator, to at least partially attenuate and/or reflect the optical pump beam and to transmit the optical idler beam; and
   a spectrometer, in optical communication with the filter, to detect plural spectral components of the optical idler beam in parallel at the second frequency so as to yield an indication of a spectroscopic measurement of the sample at the first frequency,
   wherein the first frequency is in a range from about 100 GHz to about 10 THz.

2. The system of claim 1, wherein the difference-frequency generator comprises a second-order nonlinear medium.

3. The system of claim 2, wherein the second-order nonlinear medium comprises a quasi-phase matched nonlinear medium.

4. The system of claim 2, wherein the second-order nonlinear medium comprises a waveguide to guide the signal beam and the optical pump beam.

5. The system of claim 1, wherein the signal beam co-propagates with the optical pump beam.

6. The system of claim 1, wherein the spectrometer comprises:
   a demultiplexer to map the plural spectral components of the optical idler beam to respective spatial positions; and
   a detector array, in optical communication with the demultiplexer, comprising plural detector elements arrayed at the respective spatial positions to detect respective ones of the plural spectral components of the optical idler beam.

7. A system for sensing a signal beam from a sample at a first frequency, the system comprising:
   a difference-frequency generator to mix the signal beam with an optical pump beam so as to produce an optical idler beam at a second frequency equal to a difference between the first frequency and a frequency of the optical pump beam;
   a filter, in optical communication with the difference-frequency generator, to at least partially attenuate and/or reflect the optical pump beam and to transmit the optical idler beam; and
   a spectrometer, in optical communication with the filter, to detect plural spectral components of the optical idler beam in parallel at the second frequency so as to yield an indication of a spectroscopic measurement of the sample at the first frequency, wherein the signal beam comprises at least one signal pulse having a first pulse width, and further comprising:
an optical pump source, in optical communication with the difference-frequency generator, to generate the optical pump beam having at least one pump pulse having a second pulse width greater than the first pulse width.

8. The system of claim 1, further comprising:
a source, in optical communication with the sample, to illuminate the sample with an illumination signal having a spectrum that encompasses a spectroscopic feature of the sample so as to produce the signal beam.

9. The system of claim 8, further comprising:
a processor, operably coupled to the spectrometer, to compare at least a portion of the spectrum of the illumination beam to the indication of the spectroscopic measurement.

10. The system of claim 8, further comprising:
a beam-steering element, in optical communication with the source, to scan the illumination beam over at least a portion of the sample.

11. A method of sensing a signal beam from a sample at a first frequency, the method comprising:
mixing the signal beam with an optical pump so as to produce an optical idler beam at a second frequency equal to a difference between the first frequency and a frequency of the optical pump beam;
detecting, with a spectrometer, plural spectral components of the optical idler beam in parallel at the second frequency so as to yield an indication of a spectroscopic measurement of the sample at the first frequency; and
filtering at least a portion of the optical pump beam so as to prevent the at least a portion of the optical pump from illuminating the spectrometer,
wherein the first frequency is in a range from about 100 GHz to about 10 THz.

12. The method of claim 11, wherein the mixing the signal beam with the optical pump beam comprises illuminating a second-order nonlinear medium with the signal beam and the optical pump beam.

13. The method of claim 12, wherein illuminating the second-order nonlinear medium comprises causing the signal beam to co-propagate with the optical pump beam in the second-order nonlinear medium.

14. The method of claim 12, wherein the second-order nonlinear medium comprises a quasi-phase matched nonlinear medium.

15. The method of claim 12, wherein illuminating the second-order nonlinear medium with the signal beam and the optical pump beam comprises coupling the signal beam and the optical pump into a waveguide in the second-order nonlinear medium.

16. The method of claim 11, wherein detecting the plural spectral components further comprises:
mapping the plural spectral components of the optical idler beam to respective spatial positions; and
sensing at least one of the plural spectral components with a detector element at the respective spatial position of the at least one of the plural spectral components.

17. A method of sensing a signal beam from a sample at a first frequency, the method comprising:
mixing the signal beam with an optical pump so as to produce an optical idler beam at a second frequency equal to a difference between the first frequency and a frequency of the optical pump beam;
detecting, with a spectrometer, plural spectral components of the optical idler beam in parallel at the second frequency so as to yield an indication of a spectroscopic measurement of the sample at the first frequency; and
filtering at least a portion of the optical pump beam so as to prevent the at least a portion of the optical pump from illuminating the spectrometer,
wherein the signal beam comprises at least one signal pulse having a first pulse width, and further comprising:
generating the optical pump beam to include at least one pump pulse having a second pulse width greater than the first pulse width.

18. The method of claim 11, further comprising:
illuminating the sample with an illumination beam whose spectrum encompasses a spectroscopic feature of the sample so as to produce the signal beam.

19. The method of claim 18, further comprising:
comparing at least a portion of the spectrum of the illumination beam to the indication of the spectroscopic measurement.

20. The method of claim 11, further comprising:
scanning the illumination beam over at least a portion of the sample.

* * * * *